United States Patent
Schiltges et al.

(10) Patent No.: US 9,084,848 B2
(45) Date of Patent: Jul. 21, 2015

(54) INFUSION SET WITH A MASSAGE-HUB

(75) Inventors: Gilbert Schiltges, Kirchberg (CH);
Michael Haeberli, Kussnacht (CH);
Lucas Kalt, Bern (CH)

(73) Assignee: Roche Diagnostics International AG,
Rotkreuz (CH)

( * ) Notice: Subject to any disclaimer, the term of this patent is extended or adjusted under 35 U.S.C. 154(b) by 406 days.

(21) Appl. No.: 12/270,540

(22) Filed: Nov. 13, 2008

(65) Prior Publication Data

US 2009/0234272 A1 Sep. 17, 2009

Related U.S. Application Data

(63) Continuation of application No. PCT/EP2007/002202, filed on Mar. 13, 2007.

(30) Foreign Application Priority Data

May 15, 2006 (DE) .......................... 10 2006 022 554

(51) Int. Cl.
| | |
|---|---|
| *A61N 1/30* | (2006.01) |
| *A61M 5/158* | (2006.01) |
| *A61M 5/142* | (2006.01) |
| *A61M 25/00* | (2006.01) |
| *A61N 1/04* | (2006.01) |
| *A61H 23/02* | (2006.01) |
| *A61M 5/44* | (2006.01) |
| *A61M 25/02* | (2006.01) |

(Continued)

(52) U.S. Cl.
CPC ........... *A61M 5/158* (2013.01); *A61H 23/0245* (2013.01); *A61M 5/14248* (2013.01); *A61M 25/00* (2013.01); *A61N 1/0492* (2013.01); *A61N 1/306* (2013.01); *A61H 23/02* (2013.01); *A61H 2201/0207* (2013.01); *A61H 2201/0228* (2013.01); *A61H 2201/10* (2013.01); *A61M 5/44* (2013.01); *A61M 2005/1581* (2013.01); *A61M 2025/0266* (2013.01); *A61M 2205/058* (2013.01); *A61N 1/327* (2013.01); *A61N 2005/0659* (2013.01)

(58) Field of Classification Search
CPC ................ A61M 5/158; A61M 25/00; A61M 2005/1581; A61M 2025/0266; A61M 2205/058; A61H 23/02; A61H 23/0245; A61H 2201/0207; A61H 2201/0228; A61H 2001/10; A61N 1/0492; A61N 1/306; A61N 1/327; A61N 2005/0659
USPC .............. 604/20, 288.01–288.03, 469, 21, 22
See application file for complete search history.

(56) References Cited

U.S. PATENT DOCUMENTS

| | | | | |
|---|---|---|---|---|
| 4,457,748 | A | * | 7/1984 | Lattin et al. ...................... 604/20 |
| 5,026,344 | A | * | 6/1991 | Dijkstra et al. ........... 604/288.02 |
| 5,645,526 | A | * | 7/1997 | Flower ............................ 604/20 |

(Continued)

FOREIGN PATENT DOCUMENTS

| | | |
|---|---|---|
| DE | 199 29 7133 | 1/2001 |
| JP | 2005 095473 | 4/2005 |

(Continued)

*Primary Examiner* — Edelmira Bosques
(74) *Attorney, Agent, or Firm* — Dinsmore & Shohl LLP

(57) ABSTRACT

A device and method for stimulating tissue to improve the resorption kinetics of an active substance. The device and method can include an infusion set having a main body, a cannula, and a base plate through which the cannula projects so that the cannula can puncture into a tissue of an animal to deliver the active substance.

29 Claims, 4 Drawing Sheets

(51) Int. Cl.
*A61N 1/32* (2006.01)
*A61N 5/06* (2006.01)

(56) References Cited

U.S. PATENT DOCUMENTS

| | | | |
|---|---|---|---|
| 5,857,983 A | 1/1999 | Douglas et al. | |
| 6,290,683 B1 | 9/2001 | Erez et al. | |
| 6,314,316 B1 * | 11/2001 | Gilbert et al. | 604/20 |
| 6,332,871 B1 * | 12/2001 | Douglas et al. | 600/583 |
| 6,428,491 B1 * | 8/2002 | Weiss | 601/2 |
| 6,689,100 B2 * | 2/2004 | Connelly et al. | 604/117 |
| 6,743,211 B1 * | 6/2004 | Prausnitz et al. | 604/239 |
| 6,769,969 B1 * | 8/2004 | Duescher | 451/59 |
| 6,918,901 B1 * | 7/2005 | Theeuwes et al. | 604/500 |
| 2002/0045850 A1 * | 4/2002 | Rowe et al. | 604/22 |
| 2003/0009153 A1 * | 1/2003 | Brisken et al. | 604/890.1 |
| 2003/0135154 A1 * | 7/2003 | Heiniger et al. | 604/67 |
| 2003/0144318 A1 | 7/2003 | Sallis et al. | |
| 2004/0010222 A1 * | 1/2004 | Nunomura et al. | 604/22 |
| 2004/0171980 A1 * | 9/2004 | Mitragotri et al. | 604/20 |
| 2004/0199103 A1 * | 10/2004 | Kwon | 604/46 |
| 2004/0204662 A1 | 10/2004 | Perez et al. | |
| 2007/0093728 A1 | 4/2007 | Douglas et al. | |

FOREIGN PATENT DOCUMENTS

| | | |
|---|---|---|
| WO | WO 02/091984 | 11/2002 |
| WO | WO 2004/060455 | 7/2004 |
| WO | WO 2005/104949 | 11/2005 |

* cited by examiner

INFUSION SET WITH A MASSAGE-HUB

CROSS REFERENCE TO RELATED APPLICATION

The present invention is a continuation of PCT application No: PCT/EP2007/002202 filed on Mar. 13, 2007 which claims priority to German Patent Application 102006022554.6 filed on May 15, 2006, both of which are incorporated herein in their entirety.

BACKGROUND

The present invention relates to devices for delivering, infusing, injecting, administering or dispensing a substance, and to methods of making and using such devices. More particularly, it relates to a method for stimulating tissue and to a device for this purpose.

Continuous subcutaneous insulin infusion (CSII) or pump therapy is at present a most effective form of insulin therapy for treatment of insulin-dependent diabetes.

The insulin is not injected in individual doses but is, instead, introduced into the body by a small programmable pump. The pump is located permanently or semi-permanently on the body, not in the body, and insulin is delivered via a catheter with cannula according to a programmed regimen. Insulin catheters are available in different lengths and with different needle sizes and needle materials. The following principle is applied in the administration of insulin: there is a basal supply of insulin, which is output by the pump and covers the non-dietary insulin requirement, and several so-called boluses, that is to say individual dosed releases of insulin, which can be used at meal times and to correct blood sugar values. There is usually just one type of insulin present in these pumps, either standard insulin or insulin analogs.

Pump therapy is a favorable form of insulin therapy because, in contrast to other therapies (ICT, intensive conventional insulin therapy, syringes for basal and bolus therapy, etc.), the basal rate can be more exactly controlled. An insulin pump delivers fast-acting insulin at short, regular intervals in order to achieve a uniform action. The basal rate per hour can be programmed into the pumps. Therefore, pump therapy has become a routine therapy.

In typical insulin pumps, a small motor in the insulin pump conveys the insulin out of a reservoir in the pump, through a catheter and into the subcutaneous fatty tissue, normally in the abdominal region. The pumping speed of the motor, and therefore the quantity of insulin per unit of time, can be programmed according to the patient's needs.

If, in addition to the insulin basal rate, an insulin bolus is to be released, a user can actively obtain insulin in order to lower a raised blood sugar level and/or to obtain insulin for a meal containing carbohydrates. The motor of the pump then conveys additional insulin through the catheter into the subcutaneous fatty tissue.

Such catheters comprise a plastic tube and a cannula, which extends through the skin into the subcutaneous fatty tissue. The cannulas are made, for example, of steel or plastic, for example Teflon. The catheters additionally comprise a main body which is provided on the cannula and which is secured to the skin by means of a sticking plaster or a self-adhesive cover.

In contrast to cannulas, which have to be inserted anew on each occasion, catheters of this kind for insulin therapy can remain in one place for three days, for example, before a new catheter is inserted at another site.

In the abovementioned pump therapy, it is desirable for the insulin kinetics, i.e. the time profile of the insulin concentration in the blood, to proceed as quickly as possible. For this reason, fast-acting insulin analogs are mainly used in pump therapy.

The resorption kinetics of insulin in the body depend on various factors, some of which can be influenced directly by the diabetic. For example, it is known that massaging the injection site accelerates the kinetics. This effect is used by some diabetics when administering boluses, in order to ensure a shorter interval between injecting and eating, or to bring hyperglycaemia as quickly as possible back to the euglycaemic range.

In pump therapy, massaging the injection site is difficult, and sometimes not really possible at all, since the cannula is already inserted and its means of securing does not permit access to the injection site.

Therefore, there is a need in the medical industry to have a device and a method that would facilitate massaging of the infusion site.

SUMMARY

It is against the above background that the present invention provides certain unobvious advantages and advancements over the prior art.

One object of the present invention is to make available a method and a device for stimulating tissue in order to improve resorption kinetics.

According to the present invention, an area of administration of a therapeutic substance, e.g. insulin, is stimulated to provide increased circulation, the vessels or capillaries in the tissue being stimulated to enlarge and/or to provide improved blood flow. In this way, the resorption can be increased, since the insulin from the subcutaneous fatty tissue is released into the blood vessels from the interstitial fluid and the cross-over of subcutaneously administered insulin into the blood stream (resorption) is thus accelerated.

This is achieved by dilation of the superficial capillary vessels, thereby increasing the flow of blood (hyperaemia). In this way, the resorption of insulin is also increased by virtue of an increased surface area of uptake, and a rapid action of the insulin, including fast-acting insulin, is obtained.

According another aspect of the present invention, the method can be carried out in various ways.

In one embodiment, the site of the insulin infusion, below which the insulin depot is located in the subcutaneous area, is stimulated mechanically. The mechanical stimulation imitates, simulates or replicates manual massage.

For this purpose, a vibration device that acts on the skin around the puncture site is arranged on a catheter, a catheter hub or other suitable structure associated with drug delivery, e.g. an infusion set. Such vibration devices can be based, for example, on the piezo principle known per se or can be, e.g., in the form of vibration devices that are also used in mobile phone batteries.

In another embodiment, the vibration generator is an electric motor, which moves an eccentric weight. The vibrations can be effected perpendicularly or parallel to the surface of the skin. A mechanical vibration device of this kind is also supplied with electrical energy from the infusion pump, such that a power lead is routed along and/or parallel to the catheter tube. The catheter tube and the electrical lead can be bound to each other or designed as one piece.

Since the catheters are normally exchanged or replaced after three days, it may be advantageous to provide the mechanical vibration device and the catheter with means for securing them together detachably. Such means may comprise, for example, a bayonet catch, in which case the vibration device surrounds the catheter or a main body supporting the cannula and is placed thereon before insertion of the catheter and is locked, for example, by turning. This embodiment has the advantage that, including in vibration devices that have a driven eccentric, repeat use is possible, which is justified in view of the higher production costs.

In another embodiment of the present invention that uses a piezoelectric vibration device, it may be advantageous for these to be formed fixedly on the catheter such that, in this embodiment, the lead for electrical energy is coupled to the line for the insulin. An advantage of this is that use is made convenient for a user.

It is additionally possible, for example, to stimulate the surface of the skin thermally and, in this way, to cause the vessels to dilate as a result of the heat applied to the skin. In some preferred embodiments, the catheter is designed such that a device is affixed like a plate to the skin with a self-adhesive tape, and the plate at the same time forms or supports the catheter hub. The plate accordingly has heating elements, such as resistance wires, which may be supplied with electrical energy by the pump. In this embodiment too, it is possible to have a detachably lockable design and also a one-piece or monolithic design with the catheter. A vibration device does not have to be in direct contact with the skin, and instead the vibration can be introduced into the puncture site via the catheter itself, but, in the case of a device that introduces heat, the device may be arranged directly on the skin around the puncture site.

In another embodiment, electrodes act on the skin adjacent to the puncture site, which electrodes transmit weak stimulating currents into the skin and thus lead to a stimulation of the surface of the skin. A corresponding device is also placed, for example, in a ring shape around the actual catheter and secured to it integrally or in a detachable manner, energy in this case again being supplied via the pump, via a separate module or via a current supply integrated in the device, for example by battery cells or button cells.

Instead of electrodes that emit a stimulating current, in some embodiments suitable means can be used to introduce ultrasound that act on the tissue.

In some embodiments, the device can comprise a radiating means that introduces infrared radiation, i.e. thermal radiation, into the tissue. This can be done using suitable LEDs, for example, which are arranged in a ring shape, for example.

In another embodiment, dilating substances, for example atropine, are applied to the skin or introduced into the superficial skin layers and bring about suitable dilation for a certain period of time.

In some embodiments, the device for stimulating the skin and/or tissue is controlled via the infusion pump. For this purpose, the infusion pump not only supplies the electrical energy but also comprises control functions, control being effected, for example, in such a way that the stimulation can start before the insulin is administered.

BRIEF DESCRIPTION OF THE DRAWINGS

FIG. 6 shows the device in a view from below;

Figure 1:
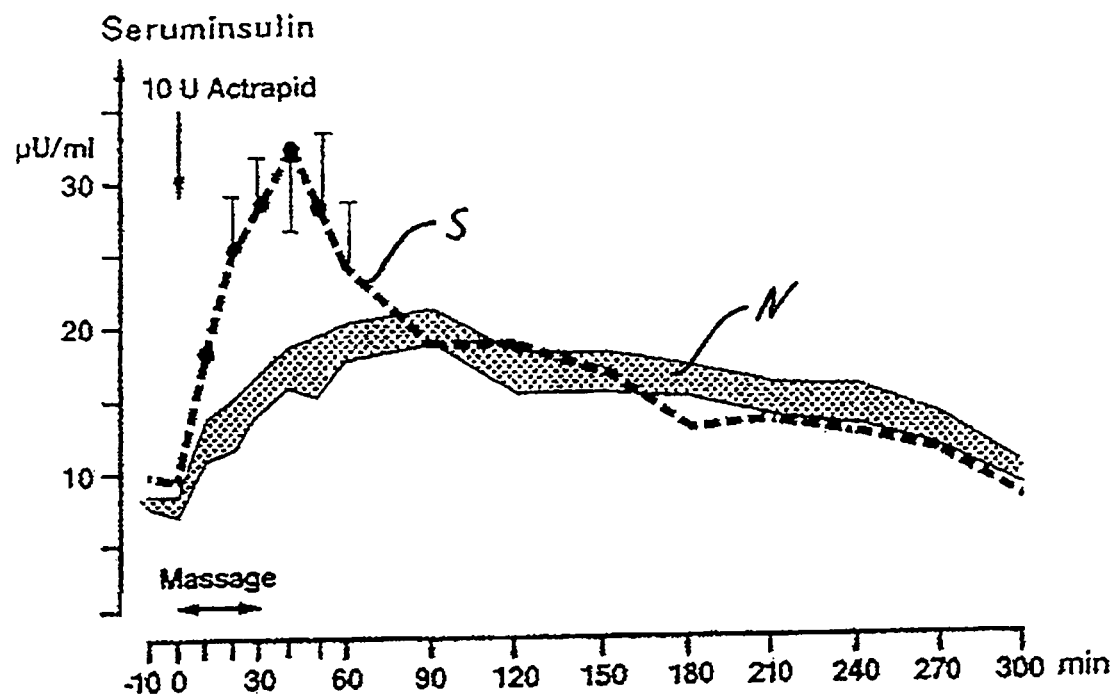
FIG. 1 is a diagram showing the serum insulin concentration in venous blood (insulin kinetics) measured upon bolus administration, with the puncture site having been stimulated, and without stimulation.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment (s) of the present invention.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the present invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc Referring to the drawings, including to FIGS. 3 and 4, a device 1 for stimulating tissue around a puncture site is arranged on a main body 2 of a catheter 3. The main body 2 has a base plate 4 from which a cannula 5 projects downwards. The cannula 5 engages through the base plate 4 and protrudes into a coupling area 6. In the coupling area 6, a passage 7 is formed which is diverted laterally and routed to the outside. The catheter 3 is attached to the outlet area 8 of the passage 7.

The catheter 3 can be guided through the coupling area 6 and formed in one piece with the cannula 5, or it can be secured releasably on the outlet 8 of the passage 7 via suitable coupling elements.

On its underside 9, the base plate 4 has a self-adhesive layer (not shown) which, after the cannula 5 has been inserted into the skin, allows the base plate 4 to be affixed to the skin in order to ensure a secure fit of the cannula 5 and of the catheter 3 on the body.

The device 1 is mounted substantially with a cross-sectional form fit onto the main body 2 and the base plate 4, in such a way that it bears on the main body 2 and on the upper face 10 opposite the underside 9.

In the case of a semicylindrical main body 2 and a circular base plate 4, for example, the device 1 bears with an underside 11 on the base plate 4, in which case a semicylindrical recess 12 is present in the underside 11 in order to receive the main body 2.

The outer shape of the device 1 is disc-shaped, for example, and the radial outer face 13 has an opening for the main body 2. In this way, the device 1 can be pushed onto the main body 2 or can be plugged onto it from above.

To secure the device 1 on the main body 2 and on the base plate 4, a self-adhesive layer can be present on the upper face 10 of the base plate 4 and/or on the underside 11 of the device 1. In another embodiment, Velcro-type or other connectors known are present on the surfaces 10, 11 to secure the device 1 there. Such securing structures or arrangements are suitable for detachable securing, if the catheter 3 is to be discarded after a certain time and the device 1 is to be reused.

It is additionally possible to provide the main body 2 and/or the base plate 4 with engagement means, such as cooperating and/or complementary locking elements, in which case the device 1 is designed with corresponding matching engagement means, such as matching locking elements. Such a lock-type connection can be designed to be permanent. If the device 1 is intended to be able to be detached, such a lock-type connection can also be actuated from outside, for example with lifting elements (not shown) which are arranged on the device 1 and disengage the locking means.

The device 1 may comprise its own energy supply in the form of an accumulator or correspondingly dimensioned cells. In addition, the device 1 can be supplied with electrical energy from outside.

For this purpose, a lead 14 is present which opens into the device 1, e.g. in the area of the catheter tube 3. In the case of a removable or detachable device 1, the lead 14 is attached via a plug connector, for example in the radial wall 13.

The lead 14 is fixedly connected to the catheter tube 3 or, if appropriate, is produced in one piece with it by means of the lead 14 being embedded in a wall of the tube 3.

If the device 1 has its own internal energy supply, the lead 14 may be used as a control lead for controlling and/or communicating with the device 1 from the infusion pump.

Figure 3:
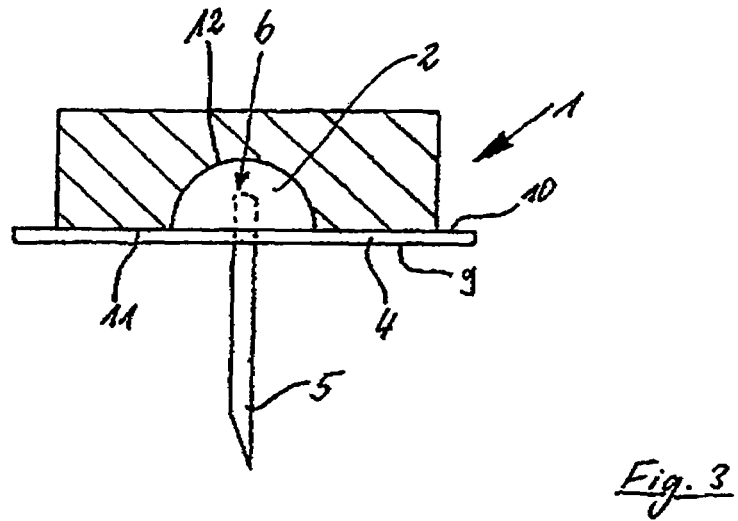
FIG. 3 is a schematic representation of one embodiment, shown partially in cross section, of a catheter with a device according to the present invention for stimulating the area surrounding a puncture site, in a view from the front.
Figure 4:
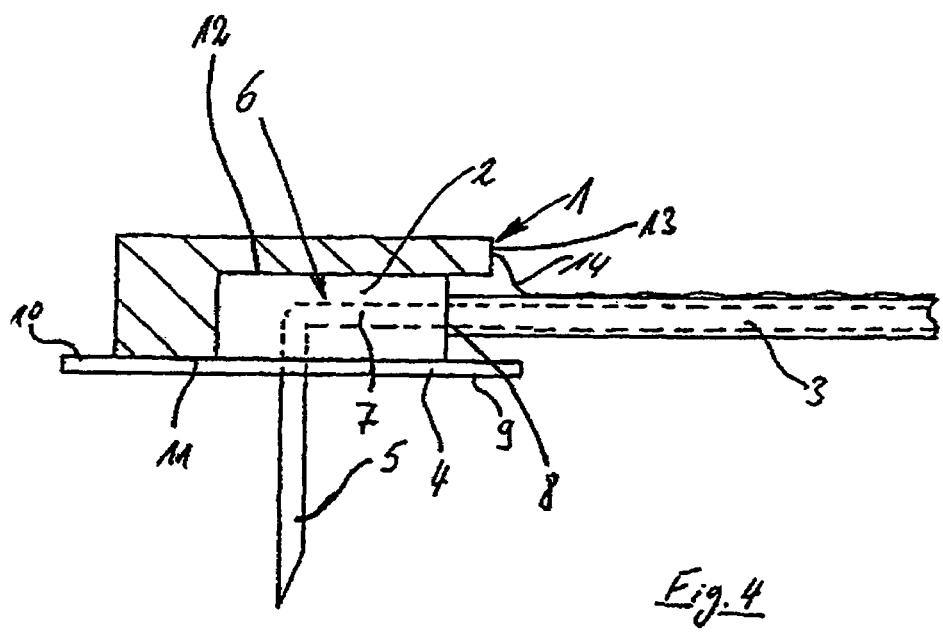
FIG. 4 shows the embodiment of the device according to FIG. 3 in a partially sectioned side view.

The embodiments described in FIG. 3 and FIG. 4 are suitable for devices 1 that stimulate the tissue by vibration and oscillation. In such arrangements of the device, it is sufficient for the vibration to be introduced into the tissue via the base plate 4. However, the device 1 can also engage laterally over the base plate 4 and bear directly on the tissue and act directly thereon.

Figure 5:
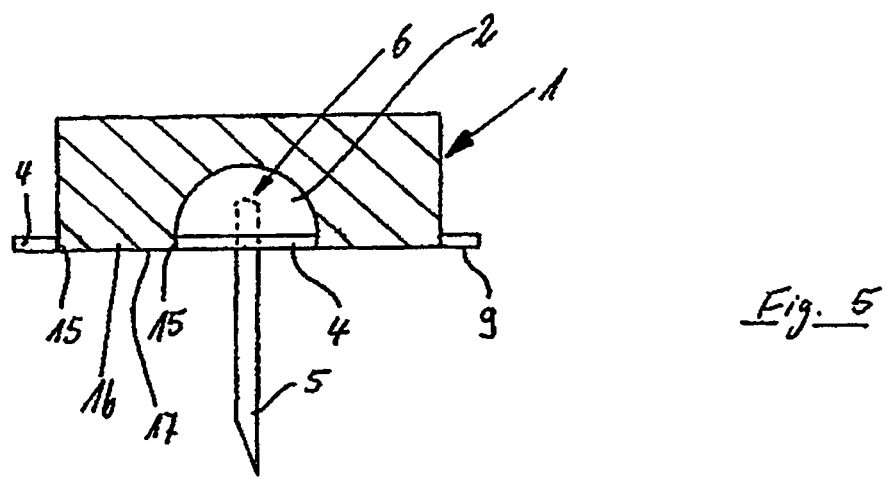
FIG. 5 shows another embodiment of the device in a partially sectioned view from the front, where the device is mounted on a main body and partially engages through the latter for direct contact with the skin.
Figure 6:
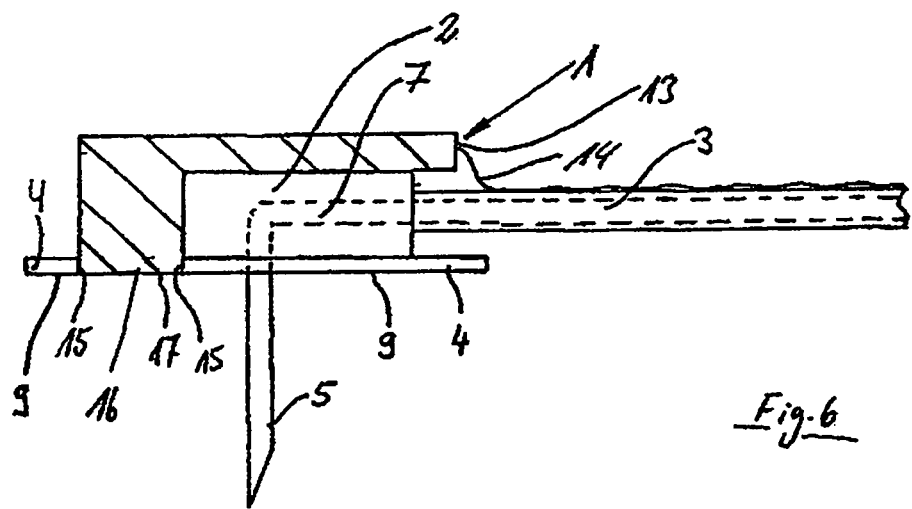
FIG. 6 shows the device according to FIG. 5 in a partially sectioned side view.
Figure 7:
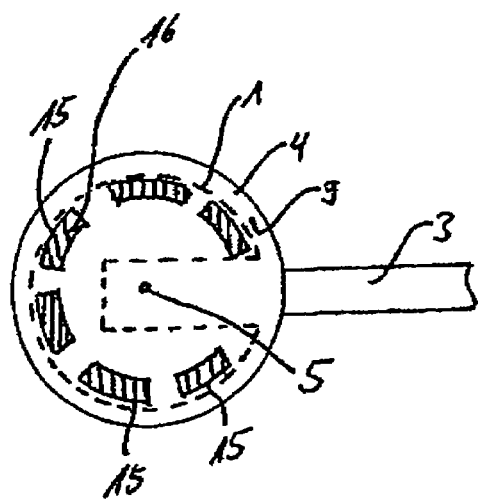
FIG. 7 shows the device according to FIG. 5.

In another embodiment as shown in FIG. 5 to FIG. 7, the base plate 4 is designed with apertures 15 (FIG. 7). The apertures 15 can be designed as sectors of a circle, a spacing being present between the apertures 15 in the circumferential direction. In addition, it is also possible to provide strip-shaped apertures 15 in conjunction with or instead of apertures 15 shaped as sectors of a circle. Projections 16 in the shape of circular segments or of other suitable shape engage through the apertures 15, in which case a bottom surface 17 of the projections 16 lies flush with the underside 9 of the plate 4.

This embodiment is suitable for devices 1 that act directly on the tissue surface with heat, ultrasound, infrared radiation or chemical substances. The projections 16 comprise, for example, resistance wires, infrared radiators or ultrasound transmitters that act on the underlying tissue.

In these embodiments too, it is conceivable for the device 1 to be integrally formed or detachable.

Figure 8:
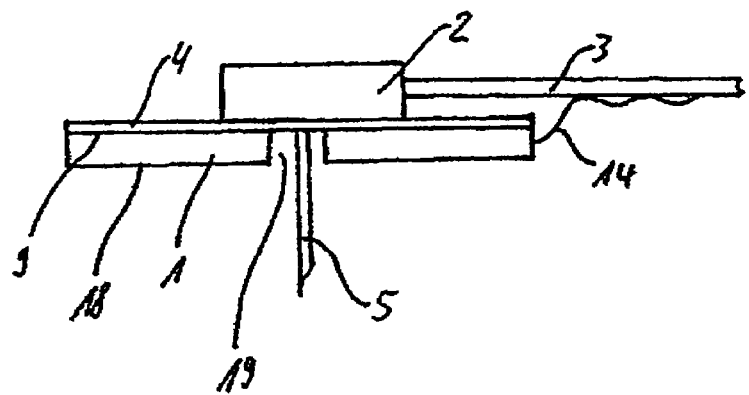
FIG. 8 shows another embodiment of the present invention.

If the device 1 is generally flat, e.g. disc-shaped (FIG. 8), it is possible for a conventional catheter 3 with its base plate 4 or its underside 9 to be affixed to a surface of the disc-shaped device 1, in which case the disc-shaped device 1 has a disc-shaped underside 18, which is also made self-adhesive. Thus, the base plate 4 is affixed indirectly to the tissue via the device 1.

In such embodiments, the device 1 has a cutout 19 which is located approximately centrally and through which the cannula 5 of the main body 2 can pass into the tissue. If appropriate, the cannula 5 is made suitably longer for use with the device 1. A lead 14 can be provided that is connected to the catheter tube 3 or runs or extends along the latter.

Such a device 1, which has a disc shape with a central recess 19, may be designed as a vibrating device 1 or as a device 1 that acts on the underlying tissue with heat, ultrasound, infrared radiation or the like.

The device 1 is not limited to one mechanism of action; the mechanisms of action, therapy and/or treatment can also be combined with one another such that vibration and/or ultrasound and/or heat and/or other forms of radiation and/or chemical substances are introduced.

Figure 2:
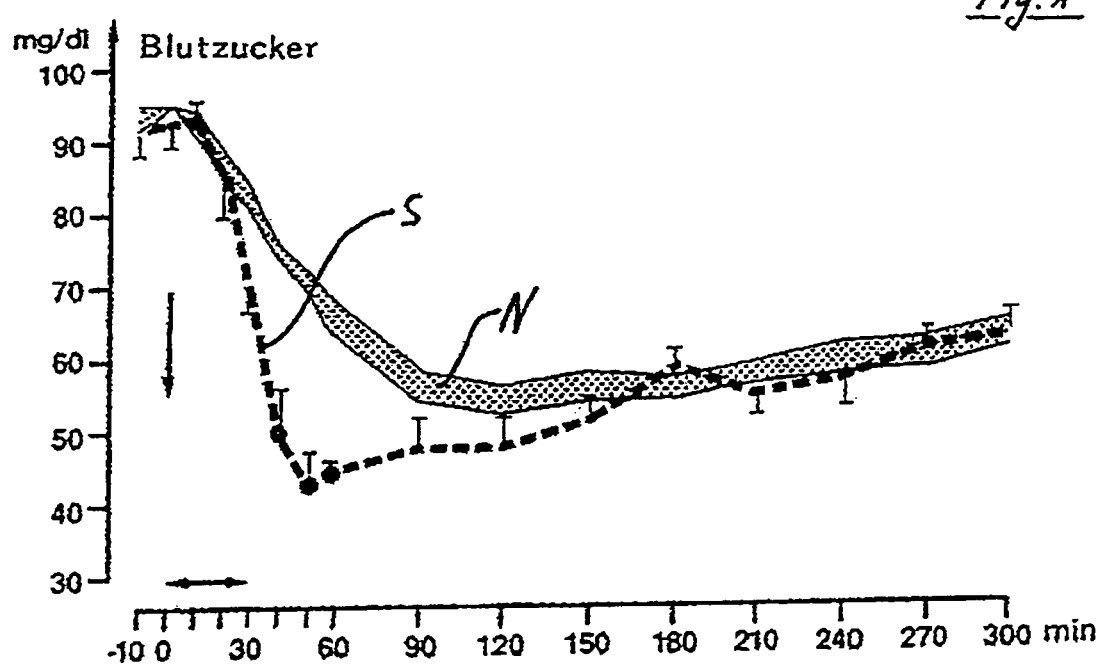
FIG. 2 is a diagram showing the blood sugar concentration profile (insulin dynamics) with skin stimulation according to the present invention, and without stimulation.

The effect of the tissue stimulation during the injection is shown in FIG. 1 and FIG. 2. FIG. 1 shows the uptake of insulin into the blood; the broken line, designated by S, shows the insulin in the venous blood, while the stippled area, designated by N, shows the normal profile without stimulation. The graph is averaged over 25 volunteers with healthy metabolism. FIG. 2 shows the blood sugar content, where the stippled area designated by N shows the decline of the blood sugar content in the venous blood without stimulation, and the broken line, designated by S, shows the drop in blood sugar when the insulin is administered with the aid of tissue stimulation.

FIG. 1 and FIG. 2 illustrate some of the advantages of aspects of the present invention, since an insulin bolus acts considerably more quickly and more effectively.

The hyperaemia (generally increased flow of blood or increased filling of part of an organ or part of the circulation with blood) of the skin brought about by the various devices in accordance with the present invention leads to accelerated pharmacokinetics (profile of the drug concentration in the body over time) and, as a result, to more rapid pharmacodynamics (pharmacological action of the drug: for example, in the case of insulin, a more rapid drop in blood glucose levels).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An infusion set for placement on a skin surface for delivering an active substance to the body of an animal and for massaging the skin surface around a puncture site to accelerate resorption of an active substance, the infusion set comprising:
a main body;
a cannula supported on the main body and protruding into a coupling area of the main body; and
a base plate through which the cannula projects such that the cannula can puncture into a tissue of the animal to deliver the active substance, wherein the base plate includes a device spaced from the cannula such that the cannula has no contact with the device which stimulates the skin surface around the puncture site of the cannula for an extended period of time of more than one minute after puncturing the tissue with the cannula to increase the flow of blood and the resorption of an administered active substance, wherein the base plate vibrates, oscillates, emits thermal radiation, or combinations thereof, to improve blood flow; and
wherein an underside of the base plate comprises apertures designed as sectors of a circle, and the underside of the base plate has projections that are directed through the apertures toward the skin surface to be stimulated, the sectors of the circle surrounding and spaced from the cannula and the sectors of the circle having a spacing present between the apertures in a circumferential direction, for the massaging of the skin surface around the puncture site to accelerate the resorption of the active substance.

2. The infusion set of claim 1, wherein the device is removably attached to the main body.

3. The infusion set of claim 1, wherein the device is designed to be connected to and detached from the main body via an adhesive layer, hook and loop fasteners, bayonet catches, cooperating locking elements or complementary locking elements.

4. The infusion set of claim 1, wherein the base plate can be mounted substantially with a cross-sectional form fit onto the main body such that it bears on the main body.

5. The infusion set of claim 1, further comprising a self-adhesive layer on an upper face of the base plate.

6. The infusion set of claim 1, wherein the device is disc-shaped, and can be pushed or plugged onto the main body.

7. The infusion set of claim 1, wherein the device further comprises an energy supply in the form of one of an accumulator and/or energy-storing cells.

8. The infusion set of claim 1, further comprising a lead coupled to the main body or the device that is configured to carry at least one of electrical energy and control signals.

9. The infusion set of claim 8, wherein the lead is one of connected to an infusion set tubing or formed in one piece with the tubing.

10. The infusion set of claim 1, wherein the projections radiate heat, transmit heat, release chemical substances, or emit electrical stimulating currents.

11. The infusion set of claim 1, wherein the device has the shape of a flat disc.

12. The infusion set of claim 1, wherein a bottom surface of the projections lies flush with the underside of the base plate.

13. The infusion set of claim 1, wherein the base plate comprises the underside for positioning on the body of the animal, the underside having an adhesive layer coupled thereto for securing the infusion set to the body of the animal.

14. The infusion set of claim 1, wherein the device is configured to stimulate the tissue around the puncture site of the cannula up to thirty minutes after puncturing the tissue with the cannula.

15. The infusion set of claim 1 wherein the cannula projects through a generally central cutout of the device defining a space having an outer perimeter, the space located between the cannula and the device, and the infusion set is configured to deliver stimulation outside of the space provided by the cutout.

16. A method of placing an infusion set on a skin surface for delivering an active substance to the body of an animal and for massaging the skin surface around a puncture site to accelerate resorption of an active substance, the method comprising:
providing the infusion set comprising:
a main body;
a cannula supported on the main body and protruding into a coupling area of the main body; and
a base plate through which the cannula projects such that the cannula can puncture into a tissue of the animal to deliver the active substance, wherein the base plate includes a device spaced from the cannula such that the cannula has no contact with the device which stimulates the skin surface around the puncture site of the cannula for an extended period of time of more than one minute after puncturing the tissue with the cannula to increase the flow of blood and the resorption of an administered active substance, wherein the base plate vibrates, oscillates, emits thermal radiation, or combinations thereof, to improve blood flow; and
wherein an underside of the base plate comprises apertures designed as sectors of a circle, and the underside of the base plate has projections that are directed through the apertures toward the skin surface to be stimulated, the sectors of the circle surrounding and spaced from the cannula and the sectors of the circle having a spacing present between the apertures in a circumferential direction, for the massaging of the skin surface around the puncture site to accelerate the resorption of the active substance; and
placing the infusion set on the skin surface, stimulating the skin surface, and infusing the active substance into the body of the animal.

17. The method of claim 16, wherein the device is removably attached to the main body.

18. The method of claim 17, wherein the device is designed to be connected to and detached from the main body via an adhesive layer, hook and loop fasteners, bayonet catches, cooperating locking elements or complementary locking elements.

19. The method of claim 16, wherein the base plate can be mounted substantially with a cross-sectional form fit onto the main body such that it bears on the main body.

20. The method of claim 16, further comprising a self-adhesive layer on an upper face of the base plate.

21. The method of claim 16, wherein the device is disc-shaped, and can be pushed or plugged onto a main body.

22. The method of claim 16, wherein the device further comprises an energy supply comprising at least one of an accumulator or energy-storing cells.

23. The method of claim 16, wherein the infusion set further comprises a lead configured for carrying at least one of electrical energy and control signals.

24. The method of claim 23, wherein the lead is one of connected to an infusion set tubing or formed in one piece with the tubing.

25. The method of claim 16, wherein the projections radiate heat, transmit heat, release chemical substances, or emit electrical stimulating currents.

26. The method of claim 16, wherein the device has the shape of a flat disc.

27. An infusion set for placement on a skin surface for delivering an active substance to the body of an animal and for massaging the skin surface around a puncture site to accelerate resorption of an active substance, the infusion set comprising:
   a main body;
   a cannula supported on the main body and protruding into a coupling area of the main body; and
   a base plate through which the cannula projects such that the cannula can puncture into a tissue of the animal to deliver the active substance, wherein the base plate includes a device spaced from the cannula such that the cannula has no contact with the device which stimulates the skin surface around the puncture site of the cannula for an extended period of time of more than one minute after puncturing the tissue with the cannula to increase the flow of blood and the resorption of an administered active substance, wherein the base plate vibrates; and
   wherein an underside of the base plate comprises apertures designed as sectors of a circle, and the underside of the base plate has projections that are directed through the apertures toward the skin surface to be stimulated, the sectors of the circle surrounding and spaced from the cannula and the sectors of the circle having a spacing present between the apertures in a circumferential direction, for the massaging of the skin surface around the puncture site to accelerate the resorption of the active substance.

28. The infusion set of claim 27, wherein the device is configured to stimulate the tissue around the puncture site of the cannula for up to thirty minutes after puncturing the tissue with the cannula.

29. An infusion set for placement on a skin surface for delivering an active substance to the body of an animal and for massaging the skin surface around a puncture site to accelerate resorption of an active substance, the infusion set comprising:
   a main body;
   a cannula supported on the main body and protruding into a coupling area of the main body;
   a base plate through which the cannula projects such that the cannula can puncture into a tissue of the animal to deliver the active substance, wherein the base plate includes a device spaced from the cannula such that the cannula has no contact with the device which stimulates the skin surface around the puncture site of the cannula for an extended period of time of more than one minute after puncturing the tissue with the cannula to increase the flow of blood and the resorption of an administered active substance, wherein the base plate vibrates, oscillates, emits thermal radiation, or combinations thereof, to improve blood flow; and
   a reservoir coupled to the infusion set, wherein the reservoir contains an amount of the active substance effective for increasing the flow of blood and being resorbed; and
   wherein an underside of the base plate comprises apertures designed as sectors of a circle, and the underside of the base plate has projections that are directed through the apertures toward the skin surface to be stimulated, the sectors of the circle surrounding and spaced from the cannula and the sectors of the circle having a spacing present between the apertures in a circumferential direction, for the massaging of the skin surface around the puncture site to accelerate the resorption of the active substance.

* * * * *